United States Patent
Mahadik et al.

(10) Patent No.: US 11,712,320 B2
(45) Date of Patent: Aug. 1, 2023

(54) METHODS AND SYSTEMS TO AUTOMATE SURGICAL INTERVENTIONS

(71) Applicant: Stryker Corporation, Kalamazoo, MI (US)

(72) Inventors: Amit Mahadik, San Jose, CA (US); Jagadish Venkataraman, San Jose, CA (US); Ramanan Paramasivan, San Jose, CA (US); Brad Hunter, Hollister, CA (US); Afshin Jila, San Jose, CA (US); Kundan Krishna, Fremont, CA (US); Hannes Rau, Milpitas, CA (US)

(73) Assignee: Stryker Corporation, Kalamazoo, MI (US)

( * ) Notice: Subject to any disclaimer, the term of this patent is extended or adjusted under 35 U.S.C. 154(b) by 845 days.

(21) Appl. No.: 15/927,543

(22) Filed: Mar. 21, 2018

(65) Prior Publication Data
US 2018/0271615 A1    Sep. 27, 2018

Related U.S. Application Data

(60) Provisional application No. 62/474,331, filed on Mar. 21, 2017.

(51) Int. Cl.
*A61B 90/00*    (2016.01)
*A61M 13/00*    (2006.01)
(Continued)

(52) U.S. Cl.
CPC ........ *A61B 90/37* (2016.02); *A61B 1/000094* (2022.02); *A61B 1/000095* (2022.02);
(Continued)

(58) Field of Classification Search
CPC .... A61B 17/320016; A61B 17/320068; A61B 5/0077; A61B 5/0071; A61B 5/0084;
(Continued)

(56) References Cited

U.S. PATENT DOCUMENTS

| 5,199,944 A | 4/1993 | Cosmescu |
|---|---|---|
| 5,740,801 A | 4/1998 | Branson |

(Continued)

FOREIGN PATENT DOCUMENTS

| EP | 2 368 484 A1 | 9/2011 |
|---|---|---|
| WO | WO 2009/105488 A2 | 8/2009 |

OTHER PUBLICATIONS

Invitation to Pay Additional Fees with Partial International Search issued in PCT/US2018/023567 dated May 28, 2018 (13 pages).
(Continued)

*Primary Examiner* — Michael F Peffley
*Assistant Examiner* — Samantha M Good
(74) *Attorney, Agent, or Firm* — Morrison & Foerster LLP

(57) ABSTRACT

A surgical system for providing an improved video image of a surgical site including a system controller that receives and processes video images to determine a video signature corresponding to a condition that interferes with a quality of the video images, with the system controller interacting with a video enhancer to enhance the video images from a video capturing device to automatically control the video enhancer to enhance the video images. The surgical system can also review the video images for a trigger event and automatically begin or stop recording of the video images upon occurrence of the trigger event.

33 Claims, 12 Drawing Sheets

(51) Int. Cl.
  *A61B 1/04*      (2006.01)
  *A61B 1/015*     (2006.01)
  *A61B 18/14*     (2006.01)
  *A61B 17/32*     (2006.01)
  *A61B 90/30*     (2016.01)
  *A61B 34/30*     (2016.01)
  *A61K 49/00*     (2006.01)
  *A61B 5/00*      (2006.01)
  *A61B 1/313*     (2006.01)
  *G06T 5/00*      (2006.01)
  *A61B 1/00*      (2006.01)
  *A61B 18/20*     (2006.01)
  *A61B 17/00*     (2006.01)
  *A61B 18/00*     (2006.01)
  *A61B 5/026*     (2006.01)

(52) U.S. Cl.
  CPC ............ *A61B 1/015* (2013.01); *A61B 1/043* (2013.01); *A61B 1/3132* (2013.01); *A61B 5/0077* (2013.01); *A61B 17/320016* (2013.01); *A61B 18/14* (2013.01); *A61B 34/30* (2016.02); *A61B 90/30* (2016.02); *A61B 90/361* (2016.02); *A61K 49/0017* (2013.01); *A61M 13/003* (2013.01); *G06T 5/001* (2013.01); *A61B 5/0071* (2013.01); *A61B 5/0084* (2013.01); *A61B 5/0261* (2013.01); *A61B 5/418* (2013.01); *A61B 18/20* (2013.01); *A61B 2017/00225* (2013.01); *A61B 2018/00595* (2013.01); *A61B 2018/00982* (2013.01); *A61B 2090/373* (2016.02); *A61B 2217/005* (2013.01); *A61B 2217/007* (2013.01); *A61B 2218/002* (2013.01); *A61B 2218/005* (2013.01); *A61B 2218/006* (2013.01); *A61B 2218/007* (2013.01); *A61B 2218/008* (2013.01); *A61B 2505/05* (2013.01)

(58) Field of Classification Search
  CPC ... A61B 5/0262; A61B 5/418; A61B 1/00009; A61B 1/00011; A61B 1/00013; A61B 1/015; A61B 1/042; A61B 1/043; A61B 1/05; A61B 1/06; A61B 1/313; A61B 90/37; A61B 90/30; A61B 90/36; A61B 90/361; A61B 2090/373; A61B 2017/320075; A61B 2017/00225; A61B 18/14; A61B 18/20; A61B 2218/002; A61B 2218/005; A61B 2218/006; A61B 2218/007; A61B 2218/008; A61M 13/003; A61M 13/00
  See application file for complete search history.

(56) References Cited

U.S. PATENT DOCUMENTS

| | | | |
|---|---|---|---|
| 6,533,721 B1* | 3/2003 | Beutter | H04N 5/217 600/167 |
| 9,066,658 B2 | 6/2015 | Hamel et al. | |
| 2008/0122924 A1* | 5/2008 | Tashiro | G16H 40/20 348/51 |
| 2008/0243054 A1 | 10/2008 | Mollstam et al. | |
| 2009/0268010 A1* | 10/2009 | Zhao | A61B 1/00009 348/45 |
| 2011/0237880 A1* | 9/2011 | Hamel | G16H 50/50 600/104 |
| 2014/0051921 A1 | 2/2014 | Miller et al. | |
| 2016/0239967 A1 | 8/2016 | Chou et al. | |

OTHER PUBLICATIONS

Society of American Gastrointestinal and Endoscopic Surgeons; "Sages 2013 Scientific Session & Postgraduate Courses—Innovating the Present for the Future—Surgical Spring Week Final Program"; pp. 1, 63 and 199; 2013 (3 pages).

Webpage screenshot of Stryker Clarity Video Enhancer; known before invention (1 page).

* cited by examiner

METHODS AND SYSTEMS TO AUTOMATE SURGICAL INTERVENTIONS

CROSS REFERENCE TO RELATED APPLICATION

This application claims priority to U.S. Provisional Application Ser. No. 62/474 331, filed Mar. 21, 2017, which is hereby incorporated by reference in its entirety.

FIELD

This disclosure relates generally to the field of medical imaging, and more particularly to providing an improved image of a surgical site for use in a surgical procedure.

BACKGROUND

In a typical endoscopic procedure, including a laparoscopic surgical procedure, smoke can be created which can interfere with an image of the surgical site being viewed. A better image during smoke creation is desired. A fast, easy and reliable method of arranging the medical or surgical devices in a medical care area is also desired.

SUMMARY

The present invention, according to various aspects, is directed to systems and methods for providing an improved video image of a surgical site. The system comprises a tool for manipulating tissue at the surgical site, a light source for providing light to the surgical site, a video capturing device for obtaining video images at the surgical site, an image display for displaying the video images, and a system controller configured to maintain quality of the video images obtained by the video capturing device and provided to the image display. The system controller receives and processes the video images to determine a video signature corresponding to a condition that interferes with a quality of the video images. The system controller interacts with a video enhancer to enhance the video images from the video capturing device to automatically control the video enhancer to enhance the video images passing from the video capturing device to the image display upon detection of the condition that interferes with the quality of the video images so that a user is free from having to control the video enhancer to obtain the improved video image of the surgical site for viewing on the image display.

Another aspect of the present invention is to provide a system for providing an improved video image of a surgical site. The system comprises a tool for manipulating tissue at the surgical site, a suction system for providing suction at the surgical site, a light source for providing light to the surgical site, a video capturing device for obtaining video images at the surgical site, an image display for displaying the video images, and a system controller configured to maintain quality of the video images obtained by the video capturing device and provided to the image display. The system controller receives and processes the video images to determine a video signature corresponding to a condition that interferes with a quality of the video images. The system controller interacting with a video enhancer, the tool, and the adjustable suction system and controlling at least one of the video capturing device, the video enhancer, the tool, and the suction system to address the condition at the surgical site to return the video images to an improved quality for viewing so that a user is free from having to control any of the video capturing device, the video enhancer, the tool, and the suction system to obtain the improved video image of the surgical site for viewing on the image display.

Yet another aspect of the present invention is to provide a method for controlling a surgical system to provide an improved image of a surgical site comprising manipulating tissue at the surgical site, illuminating the surgical site, obtaining video images at the surgical site, analyzing the video images to determine the presence of a condition that interferes with a quality of the video images, configuring a system controller to interact with a video enhancer, in response to the presence of the condition and without control from an operator, controlling the video enhancer with the system controller to generate video images having an improved image quality, and displaying the video images having the improved image quality.

Another aspect of the present invention is to provide an imaging system for viewing a video image of a surgical site. The system comprises a light source for providing light to the surgical site, a video capturing device for obtaining video images at the surgical site, a video recorder receiving the video images, and a system controller that receives and processes the video images to determine a trigger event. The system controller interacts with the video recorder to at least one of automatically recording and automatically stopping recordation of the video images upon a determination of the trigger event.

Yet another aspect of the present invention is to provide a method for controlling a surgical system that provides an image of a surgical site comprising illuminating the surgical site, obtaining video images at the surgical site, analyzing the video images to determine the presence of a trigger event, configuring a system controller to interact with a video recorder, and in response to sensing the trigger event, automatically controlling the video recorder with the system controller so that the video images are recorded.

Another aspect of the present invention is to provide a system for providing an improved video image of a surgical site. The system comprises a tool for manipulating tissue at the surgical site, a suction system for providing suction at the surgical site, a light source for providing light to the surgical site, a video capturing device for obtaining video images at the surgical site, an image display for displaying the video images, and a system controller configured to maintain or improve quality of the video images obtained by the video capturing device and provided to the image display. The system controller receives and processes the video images to determine a video signature corresponding to a condition that interferes with a quality of the video images. The system controller interacts with a video enhancer, the tool, and the suction system and controls at least one of the video capturing device, the video enhancer, the tool, and the suction system to address the condition at the surgical site to bring the video images to an improved quality for viewing so that a user is free from having to manually control any of the video capturing device, the video enhancer, the tool, and the adjustable suction system to obtain the improved video image of the surgical site for viewing on the image display. The video signature to be identified corresponds to a condition of smoke in the video images, and the system controller operates at least one of the video capturing device, the video enhancer, the cauterizing tool, the insufflator and the adjustable suction system in response to (1) smoke characteristics determined by the system controller and (2) at least one other surgical input provided to the system controller.

BRIEF DESCRIPTION OF THE DRAWINGS

One or more embodiments of the present disclosure are illustrated by way of example and should not be construed

Certain terminology will be used in the following description for convenience in reference only and will not be limiting. Said terminology will include the words specifically mentioned, derivatives thereof, and words of similar import.

DETAILED DESCRIPTION

Reference will now be made in detail to implementations and embodiments of various aspects and variations of the invention, examples of which are illustrated in the accompanying drawings. Although at least two variations of the systems, methods, uses and kits are described, other variations of the systems, methods, uses and kits may include aspects of the systems, methods, uses and kits described herein combined in any suitable manner having combinations of all or some of the aspects described.

Figure 1:
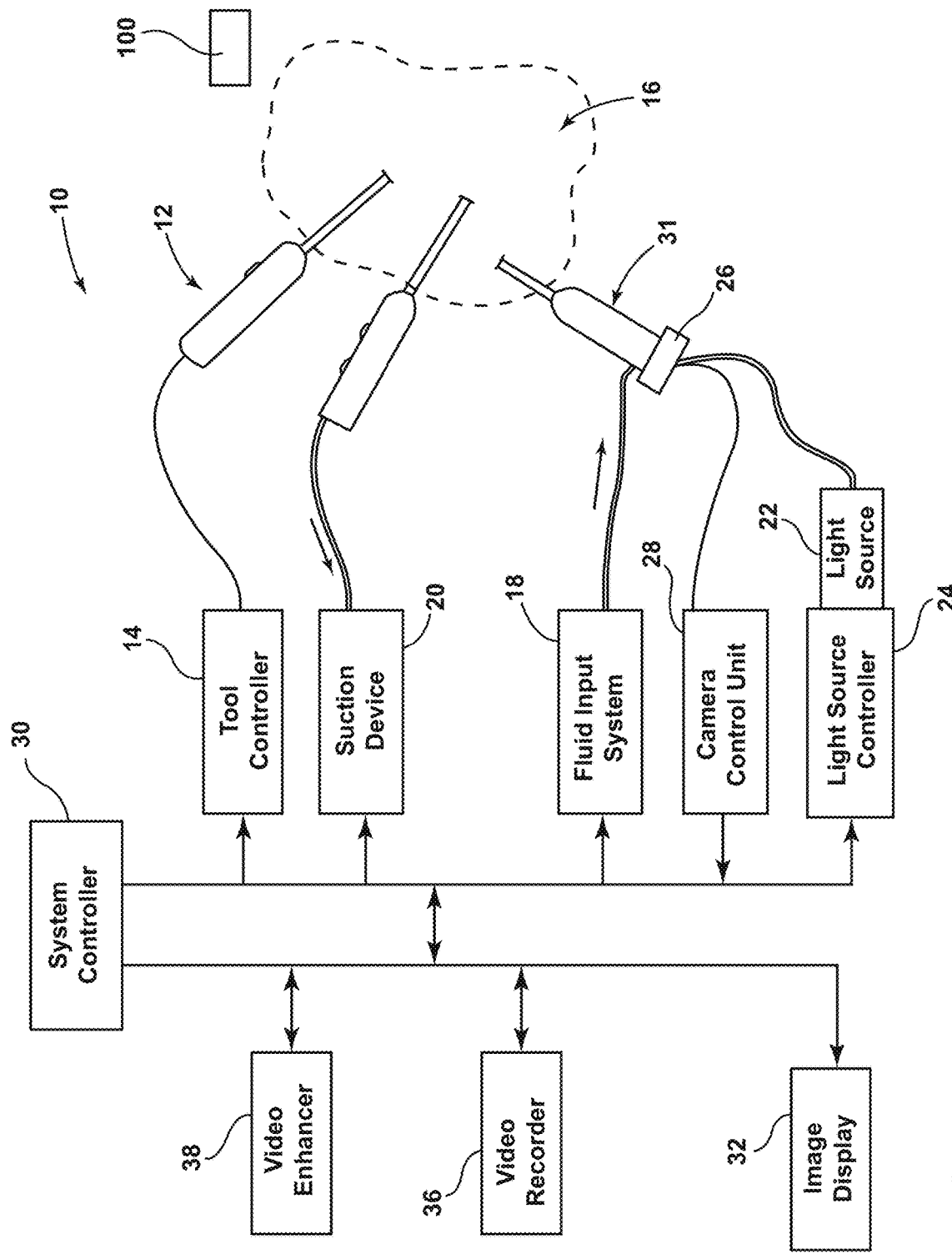
FIG. 1 illustrates a schematic view of a surgical system according to an embodiment.

FIG. 1 illustrates an embodiment of a surgical system 10 for performing a surgical procedure. The surgical system 10 may include a tool 12 under control of a tool controller 14 for manipulating tissue at a surgical site 16, a fluid input system 18 for providing a fluid to the surgical site 16, a suction system 20 (e.g., adjustable) for providing suction at the surgical site 16 for controlling removal of fluid from the surgical site 16, a light source 22 under control of a light source controller 24 for providing light to the surgical site 16, a video capturing device 26 for obtaining video signals of video images at the surgical site 16, a camera control unit 28 for controlling the video capturing device 26, and an image display 32 for displaying the video images. In the illustrated example, the tool controller 14 can be individually operated to control the tool 12, the fluid input system 18 can be individually operated to provide fluid to the surgical site 16, the suction system 20 can be individually operated to suction fluid from the surgical site 16, the light source controller 24 can be individually operated to adjust the light source 22, and/or the camera control unit 28 can be individually operated to control the video capturing device 26.

Moreover, as shown in FIG. 1, a system controller 30 communicates with the tool controller 14 to control the tool 12, with the fluid input system 18 to provide fluid to the surgical site 16, with the suction system 20 to suction fluid from the surgical site 16, with the light source controller 24 to adjust the light source 22, and with the camera control unit 28 to control the video capturing device 26. The fluid input system 18 can provide fluid to the surgical site 16 through its own device or through another device 31 (e.g., an endoscope) that also has the video capturing device 26 connected thereto and that receives light from the light source 22.

In the illustrated example, the surgical system 10 can be employed in several different surgical procedures. For example, the surgical system 10 can be used during an endoscopic procedure, including a laparoscopic procedure, wherein the tool 12 may be a cauterizing tool, the fluid input system 18 may be an insufflator for providing gas to the surgical site 16, and the suction system 20 may suction gas and potentially smoke from the surgical site 16. Alternatively, the surgical system 10 can be used during, for example, an arthroscopic procedure wherein the tool 12 may be a cutting tool, the fluid input system 18 may be a liquid pump for providing fluid (e.g., a saline solution) to the surgical site 16, and the suction system 20 may suction fluid (e.g., the saline solution and potentially blood) from the surgical site 16. It is contemplated that the procedures (e.g., the endoscopic procedures) could employ use of a robotic device or robotic devices for robotic surgery.

The illustrated surgical system 10 can also provide video images captured by the video capturing device 26 to the image display 32 to be viewed by people in an operating room. The image display 32 can be a single display or multiple displays. Furthermore, the image display 32 can be incorporated into the same housing as the housing of the system controller 30 or the housing of the system controller 30 can include another display for the video images in addition to the image display 32. The surgical system 10 can also include a video recorder 36 as a stand alone device, incorporated into the housing of the system controller 30, or in communication with the surgical system 10 from a remote location. An example of an integrated system controller 30 and video recorder 36 is the SDC3 HD Information Management System (with device control) as sold by Stryker Corporation of Kalamazoo, Mich. The video images can also be processed in a video enhancer 38 to clarify the video images before being transmitted to the image display 32, any display of the system controller 30 and the video recorder 36. The video enhancer 38 and the system controller 30 may be configured to maintain quality of the video images obtained by the video capturing device 26 and provided to the image display 32, any display of the system controller 30 and the video recorder 36. An example of the video enhancer 38 is the Clarity Video Enhancer as sold by Stryker Corporation of Kalamazoo, Mich. The video enhancer 38 can be used to adjust the video sent thereto by altering brightness, color, contrast or other features of the video to be able to better view relevant portions of the video images. For example, the video enhancer 38 can be used to alter brightness, contrast or color to be able to identify certain areas of the surgical site 16 relative to other areas of the surgical site 16 (e.g., make the contrast between smoke and adjacent areas more pronounced).

Figure 2:
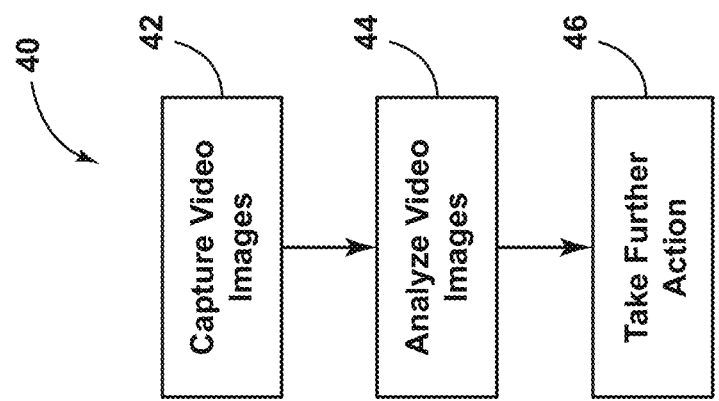
FIG. 2 illustrates a method of using the surgical system 10 according to an embodiment.

FIG. 2 illustrates a general method 40, according to an embodiment, of using the surgical system 10 as disclosed herein. As an initial step, video images are captured using the video capturing device 26 at step 42. Thereafter, the video images are analyzed to determine if a trigger condition occurs at step 44. If the trigger condition has occurred as determined at step 44, the surgical system 10 takes further action at step 46.

Figure 3:
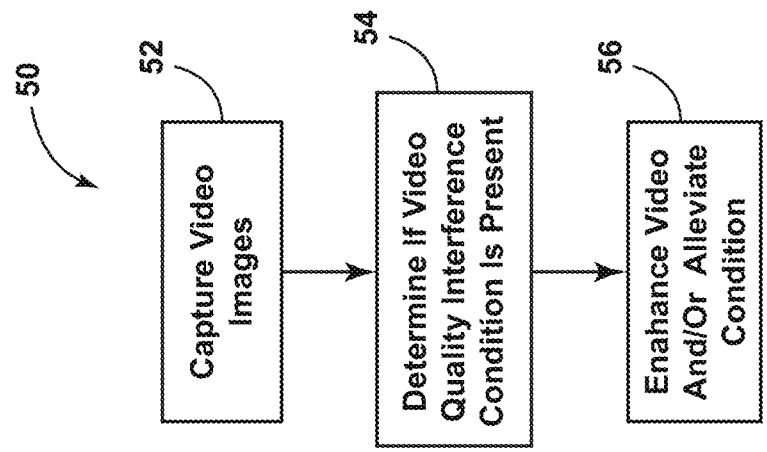
FIG. 3 illustrates a method of processing images according to an embodiment.

FIG. 3 illustrates an embodiment of the general method 40 wherein the method of FIG. 3 includes a method 50 for controlling the surgical system 10 to provide an improved image of the surgical site 16. In the method of FIG. 3, the first step includes capturing video images using the video capturing device 26 at step 52. In step 54, the video images are processed to determine if a video signature corresponding to a condition that interferes with a quality of the video images is present. If the video signature corresponding to the condition that interferes with a quality of the video images is present, system controller 30 may interact with the video enhancer 38 at step 56 to automatically control the video enhancer 38 to enhance the video images passing from the video capturing device 26. Since the system controller 30 may automatically control the video enhancer 38 at step 56 to enhance the video images passing from the video capturing device 26, a user of the surgical system 10 using the method 50 may be free from having to manually control the video enhancer 38 to obtain the improved video image of the surgical site 16. The improved video images can be displayed on the image display 32, any display of the system controller 30 and/or can be saved in the video recorder 36.

In the illustrated example, in addition to controlling the video enhancer 38, or in lieu of controlling the video enhancer 38, the system controller 30 can control the tool 12, the fluid input system 18 and/or the suction system 20 to clear the images at step 56. For example, if the surgical system 10 is used during a laparoscopic procedure, a cauterizing tool 12 can be adjusted to a lower power to produce less smoke, an insufflator 18 can be increased to add more gas to the surgical site 16, and/or the rate of suction from a suction system 20 can be increased to suction gas and potentially smoke from the surgical site 16. Alternatively, if the surgical system 10 is used during an arthroscopic procedure, a cutting tool 12 can be adjusted to a lower power to produce less blood and/or debris, a liquid pump 18 can be increased to add more surgical fluid to the surgical site 16, and/or the rate of suction from the suction system 20 can be increased to suction surgical fluid and blood from the surgical site 16.

An aspect of an embodiment is to provide the method 50 of FIG. 3 that determines when the system controller 30 should control the elements of the surgical system 10 and/or process the video images in response to smoke. The automatic detection of smoke and subsequent automation of surgical equipment (e.g., tool 12, fluid input system 18, etc.) can play a significant role in reducing or eliminating manual control of the elements of the surgical system 10 and/or manual activation of the process to clear the images, thereby reducing surgical procedure times and make performing a surgical procedure easier (and potentially reducing surgical risk and errors).

Figure 4:
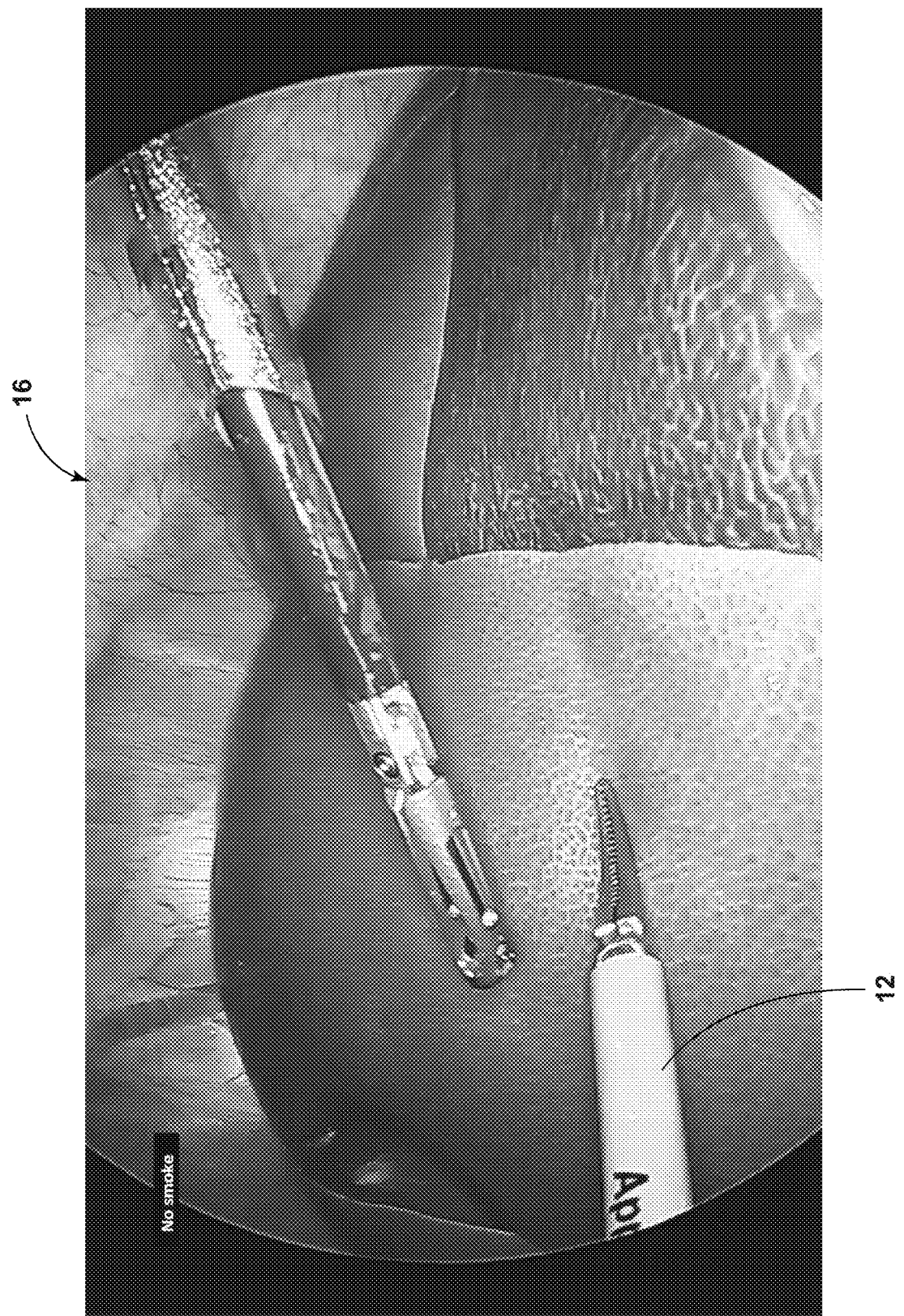
FIG. 4 is an image of an exemplary surgical site.

In the illustrated example, the step 54 of method 50 includes processing images to determine the presence and quality of smoke at the surgical site 16. As an example, during laparoscopic cholecystectomy, electrocautery, laser tissue ablation and ultrasonic (harmonic) scalpel tissue dissection, a gaseous by-product (smoke as discussed above) can be seen and smelled easily. The mean aerodynamic size of smoke particles generated varies greatly depending on the energy method used to create the smoke. FIG. 4 illustrates an example of a tool 12 being used at a surgical site 16 to create smoke (at a point in time before any smoke is present).

The step 54 of identifying smoke may be performed through analysis of the video images. In a first example, digital means can be used during an actual surgical procedure to analyze the video images (e.g., the analysis can happen a predetermined number of times per second) to record the probabilities of the state of smoke or no smoke. If the step 54 of the first example identifies that there is a probability of smoke, the method can include the further step of determining smoke density and spread based on the recorded state (smoke or no smoke) probabilities. In a second example, the video images can be analyzed to determine if smoke is present along with characteristics of the smoke (e.g., appearance or disappearance of smoke, changes in smoke intensity, changes in smoke spread, etc.) and other elements of the video (e.g., appearance or disappearance of blood and other fluids, etc.). It is contemplated that the characteristics of smoke can be determined based on input such as procedure type, camera settings and surgeon preference. The preceding list is illustrative and not exhaustive.

Figure 5:
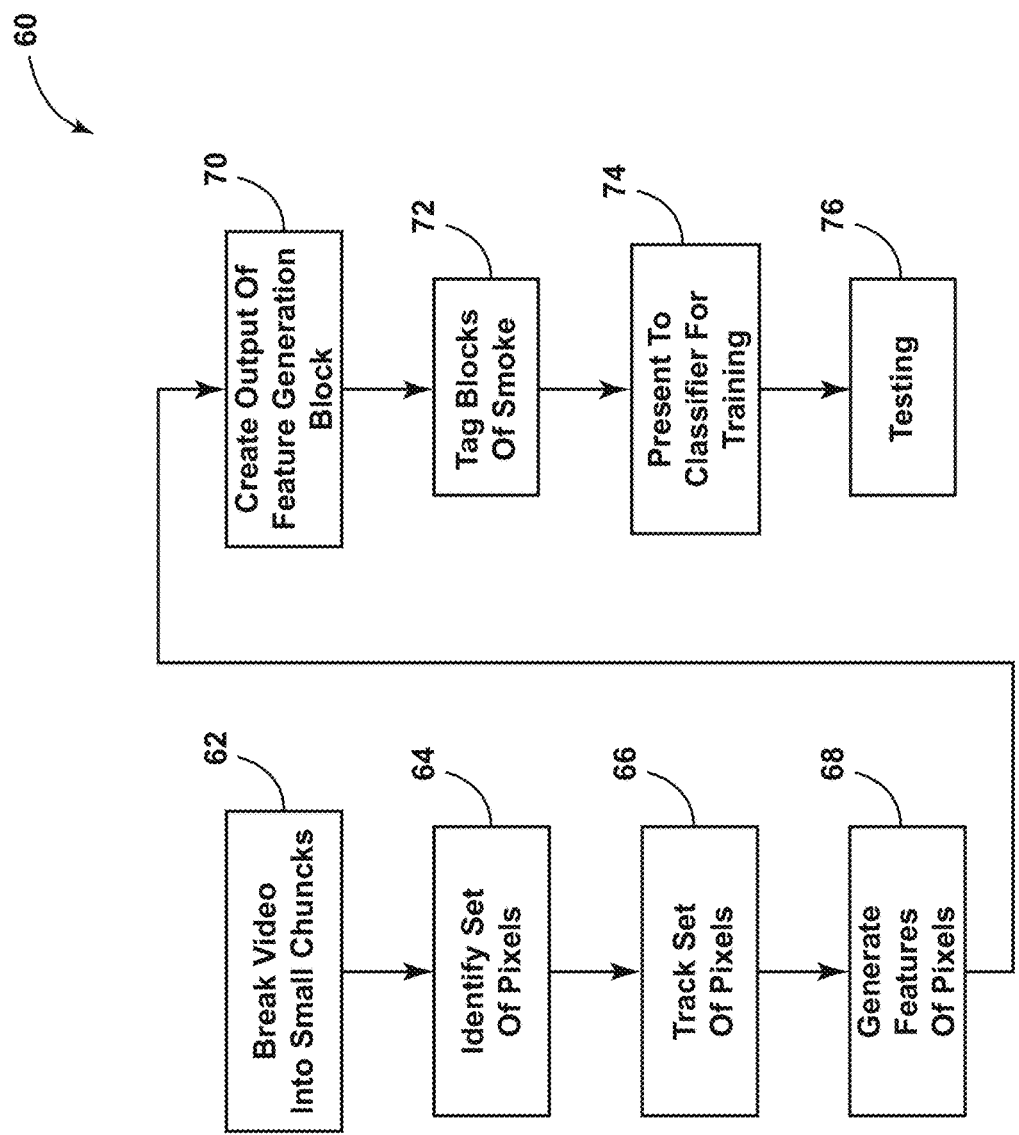
FIG. 5 illustrates a workflow process according to an embodiment.
Figure 6:
FIG. 6 is a first image of a feature tracker according to an embodiment.

FIG. 5 illustrates an embodiment of a training method 60 used to develop the process of determining the presence and quality of smoke at the surgical site 16 of step 54. The method 60 can include identifying smoke through digital means. The method 60 of identifying smoke may include a first step 62 of breaking the video image at the surgical site 16 into small chunks (e.g., a chunk of frames of a particular amount of time (e.g., one second) of video of contiguous frames or a particular number of frames (e.g., 60 frames) of video of contiguous frames). The method 60 may include an additional step 64 which is to identify a set of pixels whose convex hull in the first frame of the chunk under review can cover as much of the frame space as possible. For example, FIG. 6 shows a possible set of pixels, marked by crosses, located throughout a first frame of the chunk under review.

Figure 7:
FIG. 7 is a second image of a feature tracker according to an embodiment.
Figure 8:
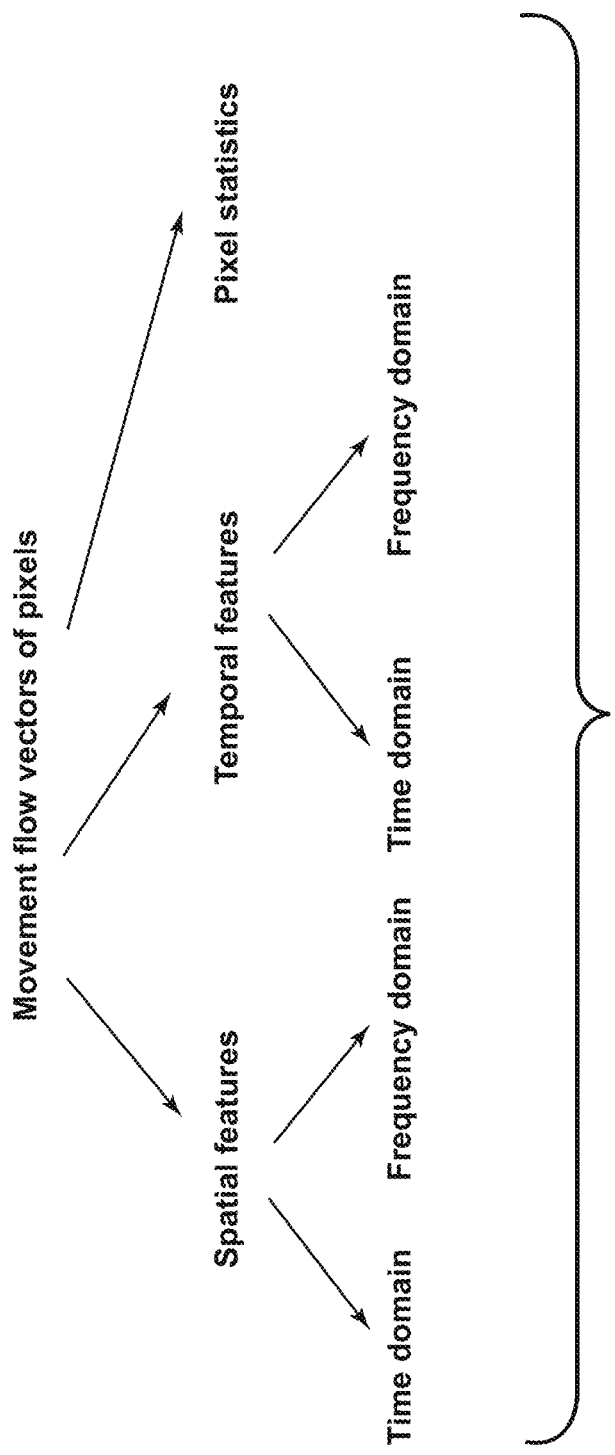
FIG. 8 is a list of possible exemplary features used according to an embodiment.
Figure 9:
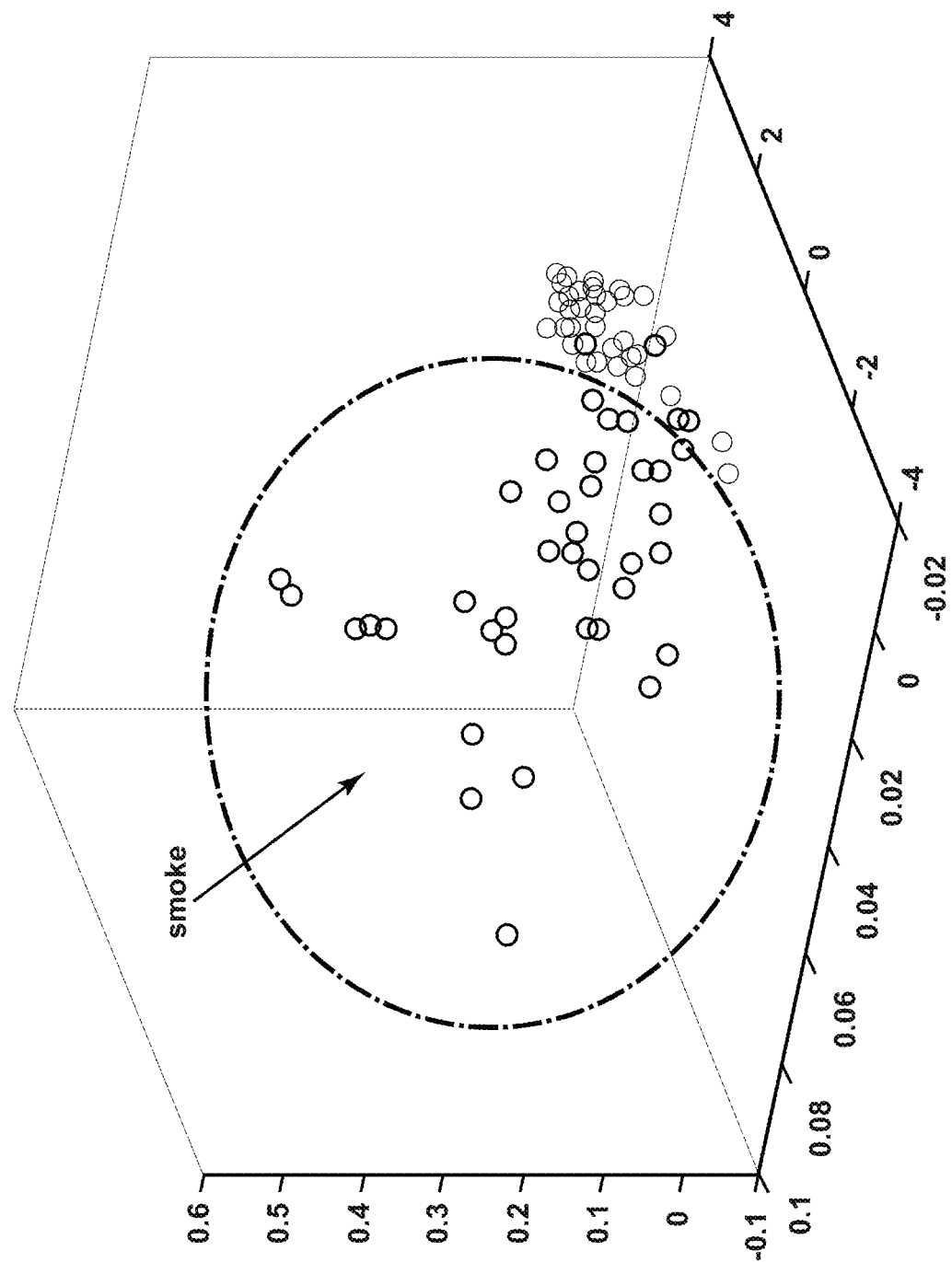
FIG. 9 illustrates a sample of 3D space determined using the process described herein in various embodiments.

In the illustrated example, a subsequent step 66 is to track the set of pixels as the set of pixels evolve from the first frame all the way to the end of the chunk of frames under review (see FIG. 7, with adjusted contrast to better illustrate the direction and magnitude of movement of a tracked pixel 67). An algorithm can be employed to track the set of pixels. For example, the Kanade Lucas Tomasi (KLT) algorithm can be employed for tracking the set of pixels. In some embodiments, tracking may yield a movement vector for each pixel in the set of tracked pixels. Given the optical flow vectors of the tracked pixels across the entire chunk, a subsequent step 68 (see FIG. 8) is to generate features of the pixels including time domain and/or frequency domain statistics of the temporal and/or spatial evolution of these pixels. Features of the pixels can include a time domain value, a frequency domain value and/or a statistical value. Examples of time domain values include (1) mean spatial displacement of one pixel across the entire chunk averaged over all pixels, (2) variance of spatial displacement of one pixel across the entire chunk averaged over all pixels, (3) entropy of pixel displacement of one pixel across the entire chunk averaged over all pixels, (4) mean angular displacement of one pixel across the entire chunk averaged over all pixels, (5) variance of angular displacement of one pixel across the entire chunk averaged over all pixels, (6) entropy of angular displacement of one pixel across the entire chunk averaged over all pixels, (7) mean spatial displacement of all tracked pixels in a given frame averaged across all frames in the chunk, (8) variance of spatial displacement of all tracked pixels in a given frame averaged across all frames in the chunk, (9) entropy of spatial displacement of all tracked pixels in a given frame averaged across all frames in the chunk, (10) mean angular displacement of all tracked pixels in a given frame averaged across all frames in the chunk, (11) variance of angular displacement of all tracked pixels in a given frame averaged across all frames in the chunk, (12) entropy of angular displacement of all tracked pixels in a given frame averaged across all frames in the chunk, (13) correlation between successive spatial displacements of one pixel across the entire chunk averaged over all pixels, (14) correlation between successive angular displacements of one pixel across the entire chunk averaged over all pixels, (15) correlation between spatial displacements of neighboring pixels in a given frame averaged across all frames in the chunk, and/or (16) correlation between angular displacements of neighboring pixels in a given frame averaged across all frames in the chunk. Examples of frequency domain values include (1) given the Fast Fourier transform (FFT) of a sequence of spatial displacements of one pixel across the entire chunk, a ratio of the energy in frequency bands 20%-40%, 40%-60%, 60%-80%, or 80%-100% of the Nyquist frequency with respect to the energy in band 0%-20%, averaged across all pixels (eg. comprising up to 4 features, with one feature from each ratio), (2) given the FFT of a sequence of angular displacements of one pixel across the entire chunk, a ratio of the energy in frequency bands 20%-40%, 40%-60%, 60%-80%, or 80%-100% of the Nyquist frequency with respect to the energy in band 0%-20%, averaged across all pixels (eg. comprising up to 4 features), (3) given the FFT of a set of spatial displacements of all tracked pixels in one frame, a ratio of the energy in frequency bands 20%-40%, 40%-60%, 60%-80%, 80%-100% of Nyquist frequency with respect to the energy in band 0%-20%, averaged across all frames in the chunk (eg. comprising up to 4 features), and (4) given the FFT of a set of angular displacements of all tracked pixels in one frame, a ratio of the energy in frequency bands 20%-40%, 40%-60%, 60%-80%, 80%-100% of the Nyquist frequency with respect to the energy in band 0%-20%, averaged across all frames in the chunk (eg. comprising up to 4 features). Examples of statistical values include (1) percentage of tracked pixels that exhibit significant motion, (2) percentage of tracked pixels that are not able to be tracked for the entire chunk of video, (3) percentage of the frame that is covered by the tracked particles across the chunk of video, and/or (4) rate of change of percentage coverage across the chunk of video. FIG. 9 illustrates a sample 3D feature space. The features can initially be hand chosen based on sample training data during construction of the system.

Figure 10:
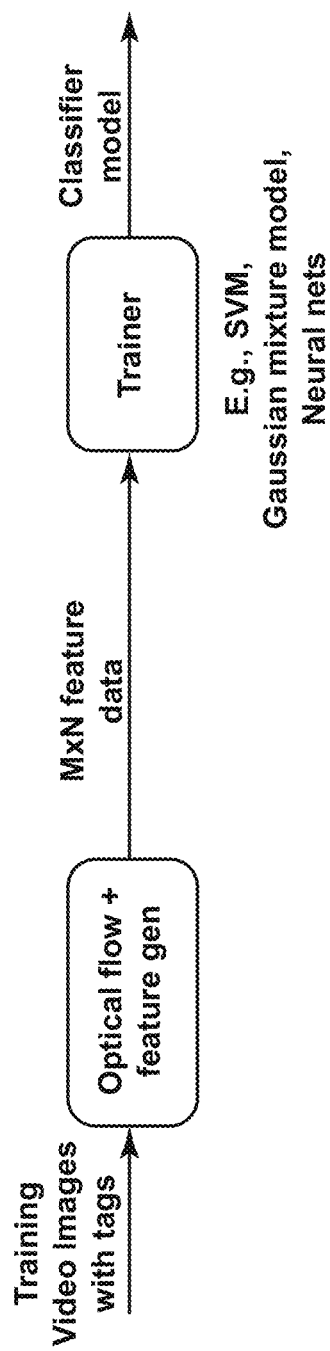
FIG. 10 illustrates the steps for classification training an embodiment.
Figure 11:
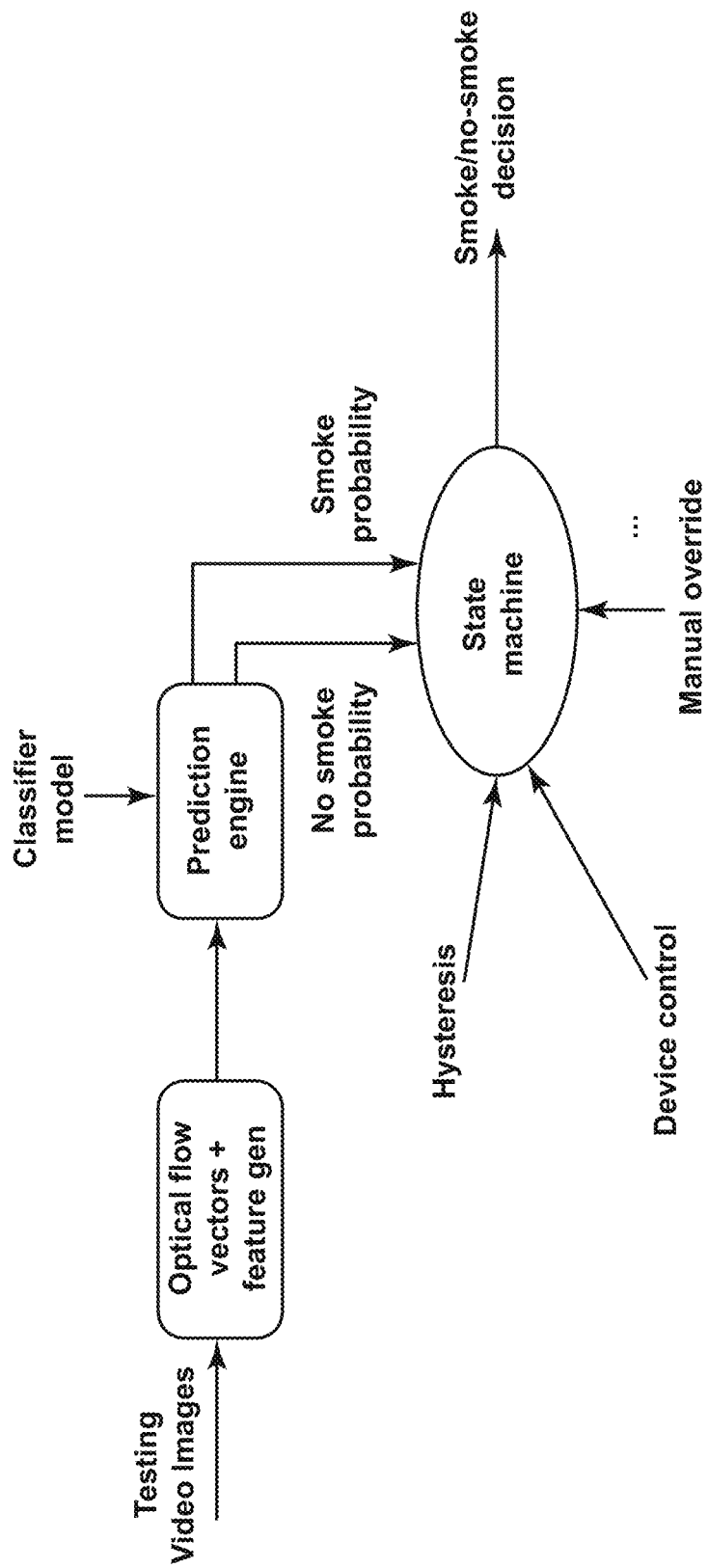
FIG. 11 illustrates the steps for classification testing an embodiment.

In the illustrated example, for every chunk of video, a subsequent step 70 includes creating an output of the feature generation block that is a vector of N numbers that represent the values of the features generated in step 68. A subsequent step 72 is to tag (e.g., manually during training of the system) which of the chunks correspond to surgical plume (smoke) being present and which ones do not, with such data being aggregated in an aggregator. The set of feature vectors from M chunks of video (M×N matrix of data) together with a M×1 vector of tags may then be presented to a trainer for training at step 74. For example, the trainer may be a kernel-based support vector machine (SVM), gaussian mixture model or neural nets. FIG. 10 illustrates the steps for classification training. Once the training is complete, the classifier model may then be applied to a set of test videos for classification testing to determine the accuracy of the prediction engine in terms of true positives, false positives, true negatives and false negatives at step 76. FIG. 11 illustrates the steps for classification testing according to an embodiment.

Returning to FIG. 3, after, the presence of smoke is determined in step 54 of the method 50 for controlling the surgical system 10 to provide an improved image of the surgical site 16, if smoke is detected the system controller 30 may automatically control the video enhancer 38 to enhance the video images passing from the video capturing device 26 and/or may automatically control other surgical devices (e.g., the tool 12 via the tool controller 14, the suction system 20, etc.) to improve the condition at the surgical site 16 at step 56. It is contemplated that step 56 could include automatically controlling the video enhancer 38 and/or the other surgical devices independently of each other or in combination with each other. For example, the suction system 20 can be controlled in tandem with controlling the video enhancer 38, with the amount of suction from the suction system 20 being tied to the amount of enhancement made by the video enhancer 38. Moreover, it is contemplated that step 56 could include automatically controlling the video enhancer 38 and/or the other surgical devices in view of the characteristics of the smoke (e.g., density, rate of spread, etc.).

In the illustrated example, domain logic can be employed to choose a type of response to clarify the image at step 56. For example, the system controller 30 can determine the manner of proceeding at step 56 after a determination of the characteristics of the smoke and video (e.g., haze, gray mean value, intensity, degree of spread of smoke, etc.), a determination of the list of surgical devices connected thereto (automatically determined upon connection and/or manually entered), a determination of procedure type (e.g., pulled automatically from a schedule database communicating with the system controller 30 or manually entered), and/or a determination of a size of porthole or natural orifice (e.g., determined by an analysis of the image from the camera unit 26 if the camera unit 26 is turned on while the insertion portion of the device 31 is being inserted into the porthole or natural orifice). The above list is illustrative and not exhaustive.

It is contemplated that the method 50 for controlling the surgical system 10 to provide an improved image of the surgical site 16 can include learning algorithms that can improve step 56 of automatically controlling the video enhancer 38 and/or the other surgical devices. For example, the system controller 30 can monitor the video enhancer 38 and/or the other surgical devices to determine if the video enhancer 38 and/or the other surgical devices are manually adjusted after the system controller 30 has automatically controlled the video enhancer 38 and/or the other surgical devices to clarify the image at step 56. If the video enhancer 38 and/or the other surgical devices are manually adjusted, the system controller 30 can adopt the domain logic steps that are employed to choose a type of response to clarify the image at step 56. For example, the system controller 30 can learn that the tool 12 was not automatically lowered in power enough because of a manual lowering of power after step 56, that the suction system 20 did not automatically provide enough suction if the suction system 20 is manually adjusted to increase suction after step 56, or that the video enhancer 36 was not automatically adjusted to a desired level if the video enhancer 38 was manually controlled after step 56. The above list is illustrative and not exhaustive. After a manual adjustment, the domain logic steps can be adjusted to correspond to the manual inventions such that the next time the method 50 is performed, the video enhancer 38 and/or the other surgical devices are automatically adjusted to the point after manual adjustment as outlined above such that the video enhancer 38 and/or the other surgical devices do not have to be manually adjusted once again. It is contemplated that the domain logic steps can be saved for a particular surgeon, a particular procedure and/or for all uses of the video enhancer 38 and/or the other surgical devices. It is further contemplated that simulations could be employed to teach and adjust the domain logic steps as outlined above.

As outlined above, the smoke detection and image enhancement procedure may allow for automatic detection of surgical smoke during tissue resection to automatically trigger digital enhancement of surgical footage and/or to trigger a mechanical smoke venting/reduction to enable the surgeon to better see an image of the surgical site 16. A goal of the aspect as discussed herein is to detect the presence of such smoke, the intensity of the smoke and the degree of spread of the smoke in the surgical video in order to be able to automatically turn on/off an image processing algorithm (e.g., in the video enhancer 38) for de-hazing as well as turn on/off or reduce power of surgical devices associated with the smoke (e.g., ventilation). Over time, the system is able to learn the preferred degree of smoke venting and de-hazing (e.g., per an individual surgeon) and automatically gravitate towards that optimal setting every time.

As outlined above, an aspect of some embodiments pertains to a centralized and automated control mechanism during minimally invasive surgery. While a smoke detection and prevention system is outlined above, another aspect of some embodiments is to use the same process with other aspects of a surgical procedure that can use a centralized and automated control mechanism during minimally invasive surgery to improve the surgery. Depending on the type of procedure, different kinds and numbers of instruments (e.g., the surgical equipment outlined above) may be connected to the system controller 30. Each of the procedures may have one or more trigger events (e.g., presence of smoke) that may warrant the activation of at least one of the instruments in different settings in order to present the surgeon with the best possible quality of surgical video that the surgeon is most comfortable viewing.

Accordingly, in the method as outlined in FIG. 3, a centralized and automatic control mechanism is used during minimally invasive surgery to improve the surgery. The trigger detection step can operate on a digital image sequence obtained from a camera (e.g., an endoscopic camera). The image sequence can be processed either in hardware (e.g., on a field programmable gate array) or in software (e.g., on a processor) using image/video processing as well as computer vision algorithms to identify the trigger event. Based on the decision of the identification of the trigger event, the domain logic configures the relevant instruments to the best known setting appropriate for the scenario. Moreover, the learning step fine tunes the values of the best known settings based on manual surgeon (or others in training) interventions. Once again, using smoke detection as an example, the first step is to identify smoke through digital means using image/video processing algorithms to pre-process the digital image/video sequence emerging from the camera (e.g., endoscopic camera) to identify relevant features and landmarks. The features and landmarks are then fed to a computer vision algorithm to make an identification of smoke along with aspects of the smoke (or absence of smoke). The algorithm can be trained using numerous training images and videos before use to be able to distinguish between various scenarios (e.g., presence or absence of smoke) with a desired level of accuracy. Based on the input of feature vectors, the algorithm can not only make a determination of whether there is smoke but can also provide a confidence metric indicating level of certainty. The algorithm can be further enhanced to quantify the intensity and/or spatial spread of surgical smoke within the visualization space. Once the presence of smoke is determined, the system controller 30 can control a device to vent the smoke, adjust the instruments causing the smoke and/or process the video image to present the best possible surgical footage to the surgeon while mitigating the effects of smoke.

While the example of smoke is outlined above, many other features and events happening during surgery can be detected using the process as outlined above in FIG. 3 and further action can be taken to enhance the surgery. For example, during sinus surgery, the surgeon can attempt to shave off nasal polyps and can encounter excess blood that smears a tip of an endoscope, thereby blocking the camera. Typically, the surgeon manually irrigates the nose using saline to clear up the scope tip and view the surgical footage again. An automatic blood detection algorithm can trigger an automatic irrigation or other tip cleaning device to eliminate the need for manual intervention by the surgeon. The amount of saline to be injected and/or the amount of tip cleaning can be learned by the algorithm over time to suit different surgeon preferences.

In an aspect of an embodiment, in addition to making the life of the surgeon easier by eliminating repetitive and manual interventions, the system can improve the quality of patient care and reduce the duration of surgery, thus saving on cost and time for everyone involved in the surgery. Furthermore, in the case of surgical smoke, the system can also reduce the surgical personnel's risk of exposure to harmful compounds like those found in the gaseous by-product of tissue dissection.

Figure 12:
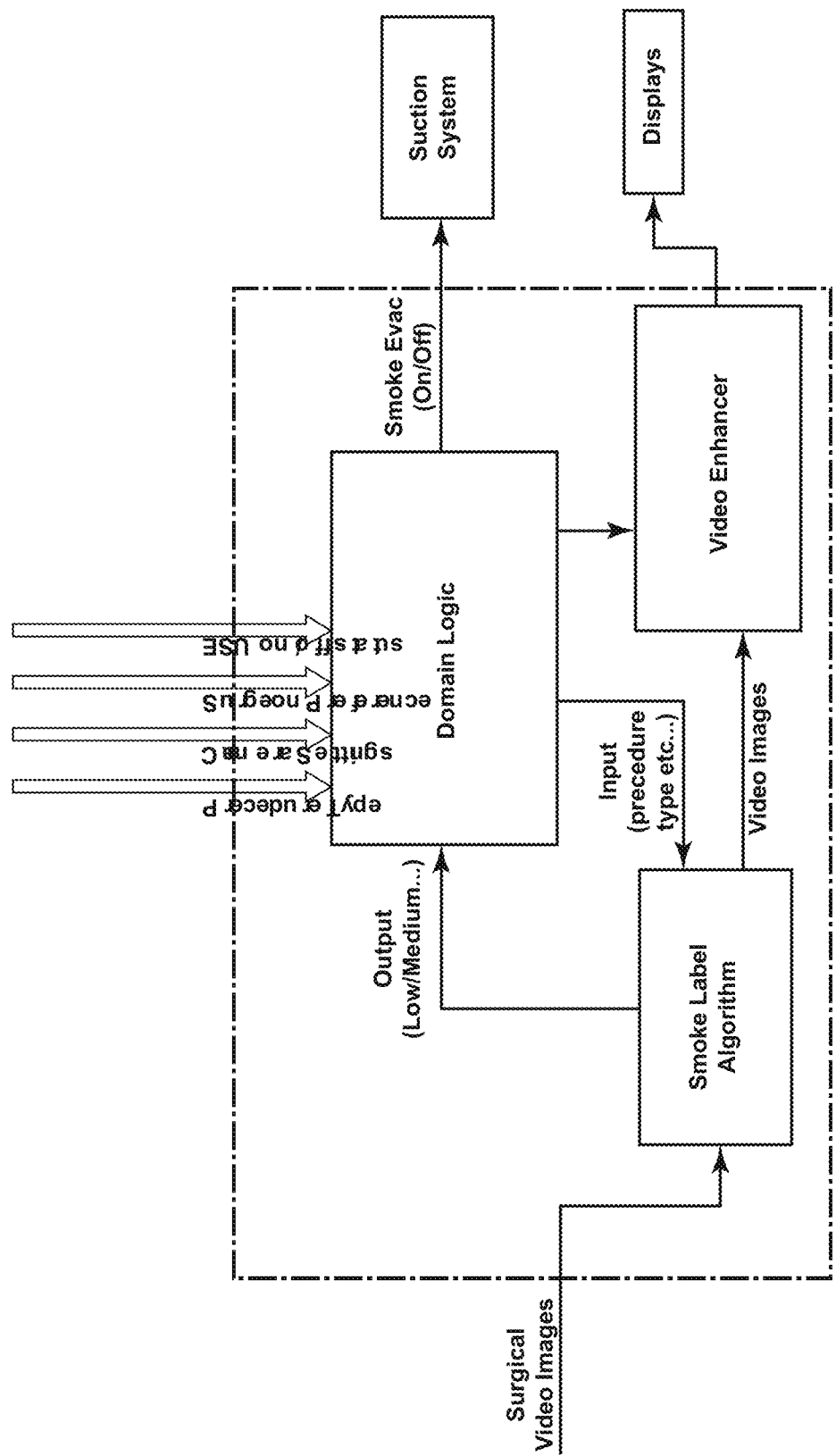
FIG. 12 illustrates a domain logic flow chart for enhancing video images depending on factors other than solely clarifying the video images according to an embodiment.

In the method 50 as outlined above, one of the main goals is to clarify the image in step 56. However, it is contemplated that step 56 could be adjusted such that the video enhancer 38 and/or the other surgical devices are activated and controlled depending on factors other than solely clarifying the image. For example, minimizing procedure completion time, patient and operating room staff health concerns, and optimal use of surgical devices can be considered during step 56 of controlling the video enhancer 38 and/or the other surgical devices. As a specific example, the system controller 30 may know from input or from a surgical schedule database that a surgical procedure will take 5 hours and a filter for the suction system 20 only has a 4 hour life when used at maximum suction. In the specific example, the suction system 20 may be reduced to not run at maximum suction to prolong the life of the filter such that step 56 is altered dependent upon a factor other than solely clarifying the image. Alternatively, if the system controller 30 knows that the procedure will take 5 hours and that the filter of the suction system 20 only has a 4 hour life when used at maximum suction, the system controller 30 can adjust the power level of the tool 12 to create less smoke such that the suction system 20 will not have to overuse the filter thereof, but still result in a clarified image at step 56 because the amount of smoke is reduced. FIG. 12 illustrates the domain logic flow chart for performing step 56 when the video enhancer 38 and/or the other surgical devices are activated and controlled depending on factors other than solely clarifying the image.

Figure 13:
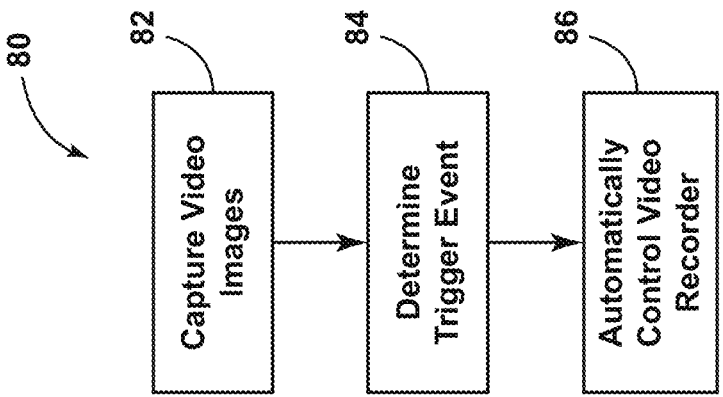
FIG. 13 illustrates a method for automatically recording video images according to an embodiment.

FIG. 13 illustrates a further embodiment of the general method 40 wherein the method of FIG. 13 includes a method 80 for automatically recording video images from the video capturing device 26. In the method of FIG. 13, the first step includes capturing video images using the video capturing device 26 at step 82. In step 84, the video images are processed to determine if a trigger event has occurred. If a trigger event has occurred, the system controller 30 automatically controls the video recorder 36 to record the video images from the video capturing device 26 or to stop the recording of the video images from the video capturing device 26 at step 86. It is contemplated that the trigger event can be any event that is at the beginning of an occasion wherein it is desirable to record the surgical procedure or any event wherein it is desirable to pause or stop a recording of the surgical procedure. For example, the video capturing device 26 can be connected to the endoscope 31. During a laparoscopic cholecystectomy surgical procedure, the endoscope 31 can pass into the body to the surgical site 16 via a trocar (not shown), with the video capturing device 26 going through certain known activities before and during insertion into the surgical site 16, such as camera white balance, passing the endoscope 31 through the trocar, first time exposure to the surgical site 16 and viewing of blood. During step 84, each of the above examples can be determined and be set as a trigger event such that when the event occurs, the video recorder 36 automatically records the video images from the video capturing device 26 at step 86. The video images will continue to be captured at step 82 looking for the next trigger event. If the next trigger event occurs (e.g., prolonged pause activity), the video recorder 36 automatically stops recording the video images from the video capturing device 26 at step 86. It is contemplated that manual intervention can be used to begin recording and method 80 can be used to automatically stop recording and that manual intervention can be used to stop recording after method 80 is used to automatically record. The method 80 can be used to automatically begin recording or stop recording multiple times during a surgical procedure. It is contemplated that method 80 can be used in combination with method 40 and method 50 (e.g., step 54 and step 84 could be the same event).

Example Imaging Agents for Use in Imaging Tissue in a Surgical Site

In various embodiments, the systems and methods described herein may be used in medical imaging comprising various optical modalities such as for example, white light imaging, fluorescence imaging (e.g., using endogenous and exogenous fluorophores), or a combination thereof. In an embodiment comprising fluorescence medical imaging applications, an imaging agent for use in combination with the method, systems, uses and kits described herein is a fluorescence imaging agent such as, for example, indocyanine green (ICG) dye. ICG, when administered to the subject, binds with blood proteins and circulates with the blood in the tissue. The fluorescence imaging agent (e.g., ICG) may be administered to the subject as a bolus injection (e.g., into a vein or an artery) in a concentration suitable for imaging such that the bolus circulates in the vasculature and traverses the microvasculature. In other embodiments in which multiple fluorescence imaging agents are used, such agents may be administered simultaneously, e.g. in a single bolus, or sequentially in separate boluses. In some embodiments, the fluorescence imaging agent may be administered by a catheter. In certain embodiments, the fluorescence imaging agent may be administered less than an hour in advance of performing the measurement of signal intensity arising from the fluorescence imaging agent. For example, the fluorescence imaging agent may be administered to the subject less than 30 minutes in advance of the measurement. In yet other embodiments, the fluorescence imaging agent may be administered at least 30 seconds in advance of performing the measurement. In still other embodiments, the fluorescence imaging agent may be administered contemporaneously with performing the measurement.

In some embodiments, the fluorescence imaging agent may be administered in various concentrations to achieve a desired circulating concentration in the blood or in other body tissue or fluid into which the fluorescence agent is administered. For example, in embodiments where the fluorescence imaging agent is ICG, it may be administered at a concentration of about 2.5 mg/mL to achieve a circulating concentration of about 5 µM to about 10 µM in blood. In various embodiments, the upper concentration limit for the administration of the fluorescence imaging agent is the concentration at which the fluorescence imaging agent becomes clinically toxic in circulating blood or other body tissue or fluid, and the lower concentration limit is the instrumental limit for acquiring the signal intensity data arising from the fluorescence imaging agent circulating with blood or in other body tissue or fluid to detect the fluorescence imaging agent. In various other embodiments, the upper concentration limit for the administration of the fluorescence imaging agent is the concentration at which the fluorescence imaging agent becomes self-quenching. For example, the circulating concentration of ICG may range from about 2 µM to about 10 mM. Thus, in one aspect, the methods described herein may comprise the step of administration of the imaging agent (e.g., a fluorescence imaging agent) to the subject and acquisition of the signal intensity data (e.g., video) prior to processing the signal intensity data. In another aspect, the method may exclude any step of administering the imaging agent to the subject.

In an embodiment, a suitable fluorescence imaging agent for use in fluorescence imaging applications alone or in combination with other imaging to generate fluorescence image data is an imaging agent which can circulate with the blood (e.g., a fluorescence dye which can circulate with, for example, a component of the blood such as lipoproteins or serum plasma in the blood) and transit vasculature of the tissue (i.e., large vessels and microvasculature), and from which a signal intensity arises when the imaging agent is exposed to appropriate light energy (e.g., excitation light energy, or absorption light energy). In some variations, the fluorescence imaging agent comprises a fluorescence dye, an analogue thereof, a derivative thereof, or a combination of these. A fluorescence dye includes any non-toxic fluorescence dye. In certain embodiments, the fluorescence dye emits fluorescence in the near-infrared spectrum. In certain embodiments, the fluorescence dye is or comprises a tricarbocyanine dye. In certain embodiments, the fluorescence dye is or comprises indocyanine green (ICG), methylene blue, or a combination thereof. In other embodiments, the fluorescence dye is or comprises fluorescein isothiocyanate, rhodamine, phycoerythrin, phycocyanin, allophycocyanin, o-phthaldehyde, fluorescamine, rose Bengal, trypan blue, fluoro-gold, or a combination thereof, excitable using excitation light wavelengths appropriate to each dye. In some embodiments, an analogue or a derivative of the fluorescence dye may be used. For example, a fluorescence dye analog or a derivative includes a fluorescence dye that has been chemically modified, but still retains its ability to fluoresce when exposed to light energy of an appropriate wavelength.

In an embodiment, the fluorescence imaging agent may be provided as a lyophilized powder, solid, or liquid. In certain embodiments, the fluorescence imaging agent may be provided in a vial (e.g., a sterile vial), which may permit reconstitution to a suitable concentration by administering a sterile fluid with a sterile syringe for use as a kit with the systems and methods described herein. Reconstitution may be performed using any appropriate carrier or diluent. For example, the fluorescence imaging agent may be reconstituted with an aqueous diluent immediately before administration. In various embodiments, any diluent or carrier which will maintain the fluorescence imaging agent in solution may be used. As an example, ICG may be reconstituted with water. In some embodiments, once the fluorescence imaging agent is reconstituted, it may be mixed with additional diluents and carriers. In some embodiments, the fluorescence imaging agent may be conjugated to another molecule, such as a protein, a peptide, an amino acid, a synthetic polymer, or a sugar, for example to enhance solubility, stability, imaging properties, or a combination thereof. Additional buffering agents may optionally be added including Tris, HCl, NaOH, phosphate buffer, and/or HEPES.

A person of skill in the art will appreciate that, although a fluorescence imaging agent was described above in detail, other imaging agents may be used in connection with the systems, methods, and techniques described herein, depending on the optical imaging modality.

In some variations, the fluorescence imaging agent used in combination with the methods, systems, uses and kits described herein may be used for blood flow imaging, tissue perfusion imaging, lymphatic imaging, or a combination thereof, or to image tissue or a body structure (anatomy) (e.g., urinary system imaging including ureter imaging) which may performed during an invasive surgical procedure, a minimally invasive surgical procedure, or a non-invasive surgical procedure in combination with invasive and minimally invasive procedures. Examples of lymphatic imaging include identification of one or more lymph nodes, lymph node drainage, lymphatic mapping, or a combination thereof. In some variations such lymphatic imaging may relate to the female reproductive system (e.g., uterus, cervix, vulva).

In some variations relating to any vascular applications, the imaging agent(s) (e.g., ICG alone or in combination with another imaging agent) may be injected intravenously. For example, the imaging agent may be injected intravenously through the central venous line, bypass pump and/or cardioplegia line and/or other vasculature to flow and/or perfuse the coronary vasculature, microvasculature and/or grafts, or other vessels. ICG may be administered as a dilute ICG/blood/saline solution down the grafted vessel or other vasculature such that the final concentration of ICG in the coronary artery or other vasculature depending on application is approximately the same or lower as would result from injection of about 2.5 mg (i.e., 1 ml of 2.5 mg/ml) into the central line or the bypass pump. The ICG may be prepared by dissolving, for example, 25 mg of the solid in 10 ml sterile aqueous solvent, which may be provided with the ICG by the manufacturer. One milliliter of the ICG solution may be mixed with 500 ml of sterile saline (e.g., by injecting 1 ml of ICG into a 500 ml bag of saline). Thirty milliliters of the dilute ICG/saline solution may be added to 10 ml of the subject's blood, which may be obtained in an aseptic manner from the central arterial line or the bypass pump. ICG in blood binds to plasma proteins and facilitates preventing leakage out of the blood vessels. Mixing of ICG with blood may be performed using standard sterile techniques within the sterile surgical field. Ten ml of the ICG/saline/blood mixture may be administered for each graft. Rather than administering ICG by injection through the wall of the graft using a needle, ICG may be administered by means of a syringe attached to the (open) proximal end of the graft. When the graft is harvested surgeons routinely attach an adaptor to the proximal end of the graft so that they can attach a saline filled syringe, seal off the distal end of the graft and inject saline down the graft, pressurizing the graft and thus assessing the integrity of the conduit (with respect to leaks, side branches etc.) prior to performing the first anastomosis. In other variations, the methods, dosages or a combination thereof as described herein in connection with cardiac imaging may be used in any vascular and/or tissue perfusion imaging applications.

Lymphatic mapping is an important part of effective surgical staging for cancers that spread through the lymphatic system (e.g., breast, gastric, gynecological cancers). Excision of multiple nodes from a particular node basin can lead to serious complications, including acute or chronic lymphedema, paresthesia, and/or seroma formation, when in fact, if the sentinel node is negative for metastasis, the surrounding nodes will most likely also be negative. Identification of the tumor draining lymph nodes (LN) has become an important step for staging cancers that spread through the lymphatic system in breast cancer surgery for example. LN mapping involves the use of dyes and/or radiotracers to identify the LNs either for biopsy or resection and subsequent pathological assessment for metastasis. The goal of lymphadenectomy at the time of surgical staging is to identify and remove the LNs that are at high risk for local spread of the cancer. Sentinel lymph node (SLN) mapping has emerged as an effective surgical strategy in the treatment of breast cancer. It is generally based on the concept that metastasis (spread of cancer to the axillary LNs), if present, should be located in the SLN, which is defined in the art as the first LN or group of nodes to which cancer cells are most likely to spread from a primary tumor. If the SLN is negative for metastasis, then the surrounding secondary and tertiary LN should also be negative. The primary benefit of SLN mapping is to reduce the number of subjects who receive traditional partial or complete lymphadenectomy and thus reduce the number of subjects who suffer from the associated morbidities such as lymphedema and lymphocysts.

Fluorescence imaging in accordance with the various embodiments may comprise use in SLN visualization, mapping, facilitates direct real-time visual identification of a LN and/or the afferent lymphatic channel intraoperatively, facilitates high-resolution optical guidance in real-time through skin and fatty tissue, visualization of blood flow, tissue perfusion or a combination thereof.

In some variations, visualization, classification or both of lymph nodes during fluorescence imaging may be based on imaging of one or more imaging agents, which may be further based on visualization and/or classification with a gamma probe (e.g., Technetium Tc-99m is a clear, colorless aqueous solution and is typically injected into the periareolar area as per standard care), another conventionally used colored imaging agent (isosulfan blue), and/or other assessment such as, for example, histology. The ICG may be packaged with aqueous solvent consisting of sterile water for injection, which is used to reconstitute the ICG. In some variations the ICG dose (mg) in breast cancer sentinel lymphatic mapping may range from about 0.5 mg to about 10 mg depending on the route of administration. In some variations, the ICG does may be about 0.6 mg to about 0.75 mg, about 0.75 mg to about 5 mg, about 5 mg to about 10 mg. The route of administration may be for example subdermal, intradermal (e.g., into the periareolar region), subareolar, skin overlaying the tumor, intradermal in the areola closest to tumor, subdermal into areola, intradermal above the tumor, periareolar over the whole breast, or a combination thereof. The NIR fluorescent positive LNs (e.g., using ICG) may be represented as a black and white NIR fluorescence image(s) for example and/or as a full or partial color (white light) image, full or partial desaturated white light image, an enhanced colored image, an overlay (e.g., fluorescence with any other image), a composite image (e.g., fluorescence incorporated into another image) which may have various colors, various levels of desaturation or various ranges of a color to highlight/visualize certain features of interest. Processing of the images may be further performed for further visualization and/or other analysis (e.g., quantification). The lymph nodes and lymphatic vessels may be visualized (e.g., intraoperatively, in real time) using fluorescence imaging systems and methods according to the various embodiments for ICG and SLNs alone or in combination with a gamma probe (Tc-99m) according to American Society of Breast Surgeons (ASBrS) practice guidelines for SLN biopsy in breast cancer patients. Fluorescence imaging for LNs may begin from the site of injection by tracing the lymphatic channels leading to the LNs in the axilla. Once the visual images of LNs are identified, LN mapping and identification of LNs may be done through incised skin, LN mapping may be performed until ICG visualized nodes are identified. For comparison, mapping with isosulfan blue may be performed until 'blue' nodes are identified. LNs identified with ICG alone or in combination with another imaging technique (e.g., isosulfan blue, and/or Tc-99m) may be labeled to be excised. Subject may have various stages of breast cancer (e.g., IA, IB, IIA).

In some variations, such as for example, in gynecological cancers (e.g., uterine, endometrial, vulvar and cervical malignancies), ICG may be administered interstitially for the visualization of lymph nodes, lymphatic channels, or a combination thereof. When injected interstitially, the protein binding properties of ICG cause it to be rapidly taken up by the lymph and moved through the conducting vessels to the SLN. ICG may be provided for injection in the form of a sterile lyophilized powder containing 25 mg ICG (e.g., 25 mg/vial) with no more than 5.0% sodium iodide. ICG may be then reconstituted with commercially available water (sterile) for injection prior to use. According to an embodiment, a vial containing 25 mg ICG may be reconstituted in 20 ml of water for injection, resulting in a 1.25 mg/ml solution. A total of 4 ml of this 1.25 mg/ml solution is to be injected into a subject (4×1 ml injections) for a total dose of ICG of 5 mg per subject. The cervix may also be injected four (4) times with a 1 ml solution of 1% isosulfan blue 10 mg/ml (for comparison purposes) for a total dose of 40 mg. The injection may be performed while the subject is under anesthesia in the operating room. In some variations the ICG dose (mg) in gynecological cancer sentinel lymph node detection and/or mapping may range from about 0.1 mg to about 5 mg depending on the route of administration. In some variations, the ICG does may be about 0.1 mg to about 0.75 mg, about 0.75 mg to about 1.5 mg, about 1.5 mg to about 2.5 mg, about 2.5 mg to about 5 mg. The route of administration may be for example cervical injection, vulva peritumoral injection, hysteroscopic endometrial injection, or a combination thereof. In order to minimize the spillage of isosulfan blue or ICG interfering with the mapping procedure when LNs are to be excised, mapping may be performed on a hemi-pelvis, and mapping with both isosulfan blue and ICG may be performed prior to the excision of any LNs. LN mapping for Clinical Stage I endometrial cancer may be performed according to the NCCN Guidelines for Uterine Neoplasms, SLN Algorithm for Surgical Staging of Endometrial Cancer; and SLN mapping for Clinical Stage I cervical cancer may be performed according to the NCCN Guidelines for Cervical Neoplasms, Surgical/SLN Mapping Algorithm for Early-Stage Cervical Cancer. Identification of LNs may thus be based on ICG fluorescence imaging alone or in combination or co-administration with for a colorimetric dye (isosulfan blue) and/or radiotracer.

Visualization of lymph nodes may be qualitative and/or quantitative. Such visualization may comprise, for example, lymph node detection, detection rate, anatomic distribution of lymph nodes. Visualization of lymph nodes according to the various embodiments may be used alone or in combination with other variables (e.g., vital signs, height, weight, demographics, surgical predictive factors, relevant medical history and underlying conditions, histological visualization and/or assessment, Tc-99m visualization and/or assessment, concomitant medications). Follow-up visits may occur on the date of discharge, and subsequent dates (e.g., one month).

Lymph fluid comprises high levels of protein, thus ICG can bind to endogenous proteins when entering the lymphatic system. Fluorescence imaging (e.g., ICG imaging) for lymphatic mapping when used in accordance with the methods and systems described herein offers the following example advantages: high-signal to background ratio (or tumor to background ratio) as NIR does not generate significant autofluorescence, real-time visualization feature for lymphatic mapping, tissue definition (i.e., structural visualization), rapid excretion and elimination after entering the vascular system, and avoidance of non-ionizing radiation. Furthermore, NIR imaging has superior tissue penetration (approximately 5 to 10 millimeters of tissue) to that of visible light (1 to 3 mm of tissue). The use of ICG for example also facilitates visualization through the peritoneum overlying the para-aortic nodes. Although tissue fluorescence can be observed with NIR light for extended periods, it cannot be seen with visible light and consequently does not impact pathologic evaluation or processing of the LN. Also, florescence is easier to detect intra-operatively than blue staining (isosulfan blue) of lymph nodes. In other variations, the methods, dosages or a combination thereof as described herein in connection with lymphatic imaging may be used in any vascular and/or tissue perfusion imaging applications.

In various embodiments, the methods, systems, uses, fluorescence agents and kits may be used for tissue perfusion imaging. Tissue perfusion relates to the microcirculatory flow of blood per unit tissue volume in which oxygen and nutrients are provided to and waste is removed from the capillary bed of the tissue being perfused. Tissue perfusion is a phenomenon related to but also distinct from blood flow in vessels. Quantified blood flow through blood vessels may be expressed in terms that define flow (i.e., volume/time), or that define speed (i.e., distance/time). Tissue blood perfusion defines movement of blood through micro-vasculature, such as arterioles, capillaries, or venules, within a tissue volume. Quantified tissue blood perfusion may be expressed in terms of blood flow through tissue volume, namely, that of blood volume/time/tissue volume (or tissue mass). Perfusion is associated with nutritive blood vessels (e.g., micro-vessels known as capillaries) that comprise the vessels associated with exchange of metabolites between blood and tissue, rather than larger-diameter non-nutritive vessels.

An embodiment includes a kit for imaging tissue in a surgical site, with the kit comprising a fluorescence imaging agent 100 and the system of FIG. 1 as used in any of the methods described herein. A further embodiment includes use of the kit of the preceding sentence for lymphatic imaging, blood flow imaging, tissue perfusion imaging, tissue anatomy imaging, or a combination thereof. Another embodiment includes a fluorescence imaging agent 100 for use with the surgical system of FIG. 1 for imaging tissue in a surgical site 16 along with employing any of the methods described herein. A further embodiment includes the fluorescence imaging agent 100 of the preceding sentence, wherein imaging tissue in the surgical site comprises imaging blood flow, tissue perfusion, lymphatic tissue, tissue anatomy, or a combination thereof. Another embodiment includes a fluorescence imaging agent 100 for use with any of the methods of FIG. 2, 3 or 13 for imaging tissue in a surgical site. A further embodiment includes the fluorescence imaging agent 100 of the preceding sentence, wherein imaging tissue in the surgical site comprises imaging blood flow, tissue perfusion, lymphatic tissue, tissue anatomy, or a combination thereof. Another embodiment includes use of the system of FIG. 1 for lymphatic imaging, blood flow imaging, tissue perfusion imaging, tissue anatomy imaging, or a combination thereof, along with employing any of the methods described herein. A further embodiment includes use of the methods of FIG. 2, 3 or 13 for lymphatic imaging, blood flow imaging, tissue perfusion imaging, tissue anatomy imaging, or a combination thereof.

While the present disclosure has been illustrated and described in connection with various embodiments shown and described in detail, it is not intended to be limited to the details shown, since various modifications and structural changes may be made without departing in any way from the scope of the present disclosure. Various modifications of form, arrangement of components, steps, details and order of operations of the embodiments illustrated, as well as other embodiments of the disclosure may be made without departing in any way from the scope of the present disclosure, and will be apparent to a person of skill in the art upon reference to this description. It is therefore contemplated that the appended claims will cover such modifications and embodiments as they fall within the true scope of the disclosure. For the purpose of clarity and a concise description features are described herein as part of the same or separate embodiments, however, it will be appreciated that the scope of the disclosure includes embodiments having combinations of all or some of the features described. For the terms "for example" and "such as," and grammatical equivalences thereof, the phrase "and without limitation" is understood to follow unless explicitly stated otherwise. As used herein, the singular forms "a", "an", and "the" include plural referents unless the context clearly dictates otherwise.

What is claimed is:

1. A system for enhancing quality of a video image of a surgical site during a surgical procedure, comprising:
   a video capturing device and camera control unit for generating and outputting video of the surgical site;
   a video enhancer configured to enhance at least some of the video output by the camera control unit for passing to an image display; and
   a system controller configured to receive at least one video frame from the camera control unit, detect a reduction in quality of the at least one video frame, and automatically control the video enhancer to enhance the at least one video frame from the camera control unit for passing to the image display upon detection of the reduction in quality of the at least one video frame so that a user is free from having to control the video enhancer to enhance quality of the at least one video frame of the surgical site for viewing on the image display during the surgical procedure.

2. The system of claim 1, further comprising:
   an insufflator for providing gas to the surgical site; and
   a suction system for providing suction at the surgical site for controlling removal of gas from the surgical site; and
   a tool for manipulating tissue at the surgical site, wherein the tool is a cauterizing tool.

3. The system of claim 2, wherein:
   the system controller interacts with the tool, the insufflator and the suction system; and
   the system controller further automatically controls at least one of the tool, the insufflator and the suction system to address a condition at the surgical site that is associated with the reduction in quality of the at least one video frame.

4. The system of claim 3, wherein:
   the reduction in quality corresponds to the condition of smoke in the at least one video frame, and the system controller operates at least one of the tool, the insufflator and the suction system in response to an amount of smoke sensed.

5. The system of claim 1, wherein:
   the reduction in quality corresponds to the condition of smoke in the at least one video frame.

6. The system of claim 1, wherein:
   the reduction in quality corresponds to the condition of blood in the at least one video frame.

7. The system of claim 1, further comprising:
   a liquid pump system for providing fluid to the surgical site; and
   a suction system providing suction for controlling removal of fluid from the surgical site; and
   a tool for manipulating tissue at the surgical site, wherein the tool is a cutting tool.

8. The system of claim 1, wherein the system comprises a light source for providing light to the surgical site.

9. The system of claim 8, wherein the system comprises the image display.

10. A system for enhancing quality of a video image of a surgical site during a surgical procedure, comprising:
    a tool for manipulating tissue at the surgical site;
    a suction system for providing suction at the surgical site;
    a light source for providing light to the surgical site;
    a video capturing device and camera control unit for generating and outputting video of the surgical site;
    an image display for displaying the video images;
    a video enhancer configured to enhance at least some of the video output by the camera control unit for passing to the image display; and
    a system controller configured to receive at least one video frame from the camera control unit, detect a reduction in quality of the at least one video frame, automatically control the video enhancer to enhance the at least one video frame from the camera control unit for passing to the image display upon detection of the reduction in quality of the at least one video frame, and automatically control at least one of the tool and the suction system to address a condition at the surgical site that interferes with quality of the video images so that a user is free from having to manually control any of the video capturing device, the video enhancer, the tool, and the suction system to respond to the reduction in quality of the video images during the surgical procedure.

11. The system of claim 10, further comprising:
an insufflator for providing gas to the surgical site; and
wherein the tool is a cauterizing tool.

12. The system of claim 11, wherein:
the system controller further automatically controls the insufflator to address the condition at the surgical site.

13. The system of claim 10, wherein:
the reduction in quality corresponds to the condition of smoke in the video.

14. The system of claim 10, wherein:
the reduction in quality corresponds to the condition of blood in the video.

15. The system of claim 10, further comprising:
a liquid pump system for providing fluid to the surgical site;
wherein the tool is a cutting tool.

16. A method for controlling a surgical system during a surgical procedure based on imaging of a surgical site, comprising:
illuminating the surgical site;
obtaining video at the surgical site by a video capturing device and camera control unit;
analyzing at least one video frame of the video received by a system controller from the camera control unit to detect a reduction in quality of the at least one video frame;
controlling, by the system controller, a video enhancer to enhance the at least one video frame from the camera control unit in response to the system controller detecting a reduction in quality of the at least one video frame without control from an operator; and
displaying at least one enhanced video frame during the surgical procedure.

17. The method of claim 16, further comprising:
providing gas to the surgical site with an insufflator; and
providing suction at the surgical site with a suction system.

18. The method of claim 17, further comprising:
automatically controlling at least one of a cauterizing tool, the insufflator and the suction system to address a condition at the surgical site associated with reduction in video image quality.

19. The method of claim 16, further comprising:
providing fluid to the surgical site; and
providing suction for controlling removal of fluid from the surgical site.

20. The method of claim 16, wherein the video is obtained during lymphatic imaging, blood flow imaging, tissue perfusion imaging, tissue anatomy imaging, or a combination thereof.

21. The method of claim 16, wherein the video is obtained during robotic surgery.

22. An imaging system for viewing a video image of a surgical site, comprising:
a video capturing device for obtaining video images at the surgical site;
a video recorder receiving the video images; and
a system controller configured to receive and process the video images to determine at least one activity captured in the video images that indicates a beginning of a use of the video capturing device to view the surgical site or a pause in use of the video capturing device to view the surgical site;
the system controller configured to interact with the video recorder to at least one of automatically record and automatically stop recordation of the video images upon determining that the at least one activity captured in the video images has occurred.

23. The system of claim 22, further including:
a tool for manipulating tissue at the surgical site.

24. The system of claim 22, wherein the system comprises a light source for providing light to the surgical site.

25. A method for controlling a surgical system that provides an image of a surgical site, comprising:
illuminating the surgical site;
obtaining video images at the surgical site;
analyzing the video images, by a system controller, to determine an occurrence of at least one activity captured in the video images that indicates a beginning of a use of the video capturing device to view the surgical site or a pause in use of the video capturing device to view the surgical site; and
in response to determining that the at least one activity captured in the video images has occurred, automatically controlling a video recorder by the system controller to record or stop recording the video images.

26. The method of claim 25, further including:
manipulating tissue at the surgical site with a tool.

27. A system for enhancing the quality of a video image of a surgical site, comprising:
a video capturing device for obtaining video at the surgical site; and
a system controller configured to maintain or improve quality of the video obtained by the video capturing device and provided to an image display, wherein the system controller is configured to receive and process the video to:
determine whether smoke that interferes with a quality of the video images is present in at least one video frame of the video and, when smoke is present in the at least one video frame, determine at least one of changes in smoke intensity and changes in smoke spread in the at least one video frame;
wherein the system controller is configured to interact with a video enhancer, a tool, and a suction system and controlling at least one of the video capturing device, the video enhancer, the tool, and the suction system to enhance the video images received from the video capturing device or to address the condition at the surgical site so that a user is free from having to manually control any of the video capturing device, the video enhancer, the tool, and the suction system to respond to the condition that interferes with the quality of the video images;
wherein the system controller is configured to determine a type of control of at least one of the video capturing device, the video enhancer, the tool, and the suction system based on (1) the at least one of changes in smoke intensity and changes in smoke spread determined by the system controller and (2) at least one other surgical input provided to the system controller.

28. The system of claim 27, wherein:
the at least one other surgical input includes characteristics of at least one of the tool, the suction system, the light source and the video capturing device.

29. The system of claim 27, wherein:
the at least one other surgical input includes a surgical procedure type.

30. The system of claim 27, wherein:
the at least one other surgical input includes surgeon preferences.

31. The system of claim 27, wherein the system comprises a light source for providing light to the surgical site.

32. The system of claim 31, wherein the system comprises the image display.

33. A kit for imaging tissue in a surgical site, the kit comprising a fluorescence imaging agent and the system of claim 1.

* * * * *